United States Patent [19]
Rosen et al.

[11] 4,228,805
[45] Oct. 21, 1980

[54] METHOD OF MEASURING BLOOD PERFUSION

[75] Inventors: Arye Rosen, Cherry Hill; William P. Santamore, Medford, both of N.J.

[73] Assignee: RCA Corporation, New York, N.Y.

[21] Appl. No.: 958,605

[22] Filed: Nov. 8, 1978

[51] Int. Cl.³ .............................................. A61B 5/02
[52] U.S. Cl. ..................................... 128/691; 128/736
[58] Field of Search ............... 128/653, 664, 691, 736, 128/742, 804

[56] References Cited

U.S. PATENT DOCUMENTS

| | | | |
|---|---|---|---|
| 3,877,463 | 4/1975 | Cary et al. | 128/736 |
| 4,080,959 | 3/1978 | Leveen | 128/736 |

FOREIGN PATENT DOCUMENTS

| | | | |
|---|---|---|---|
| 1121274 | 1/1962 | Fed. Rep. of Germany | 128/691 |
| 2530834 | 2/1977 | Fed. Rep. of Germany | 128/691 |

OTHER PUBLICATIONS

Harding, D. C., et al., *Med.& Biol. Engng.,* vol. 5, 1967, pp. 623-626.
Grayson, J., et al., *Journ. of Applied Phys.,* 30, No. 2, Feb. 1971, pp. 251-257.
Grayson, J., *Nature,* 215, 1967, pp. 767-768.
Schmidt, C. F., et al., *Am. J. Physiol.,* 108, 1934, pp. 241-263.
Gibbs, F. A., *Proc. of Soc. of Exper. Biol. & Med.,* 31, 1933, pp. 141-147.
*Electronics,* vol. 49, No. 14, Jul. 8, 1976, p. 8E.

*Primary Examiner*—Kyle L. Howell
*Attorney, Agent, or Firm*—H. Christoffersen; Samuel Cohen; Robert L. Troike

[57] ABSTRACT

A method of measuring fluid perfusion of tissue by irradiating the tissue with microwave energy of a predetermined rate, amplitude and frequency to uniformly heat a given volume of said tissue, interrupting the irradiation and measuring the rate of temperature decay of said given volume of tissue as a measure of fluid perfusion of the given volume of tissue.

4 Claims, 3 Drawing Figures

METHOD OF MEASURING BLOOD PERFUSION

CROSS REFERENCE TO RELATED APPLICATIONS

Of interest are the following pending U.S. Patent Applications: Ser. No. 859,856, filed by R. Paglione on Dec. 12, 1977, and Ser. No. 808,292 filed by F. Sterzer on June 20, 1977.

BACKGROUND OF THE INVENTION

1. Field of the Invention

This invention relates to a method for determining fluid perfusion of tissue by the use of microwave energy.

2. Description of the Prior Art

Researchers in medical science have known that the rate of blood flow within a tissue can be measured by a process of heating a device, such as a probe, which is in contact with the tissue being examined, and then recording the temperature changes by a thermocouple positioned in or near the probe. The recorded temperature changes are representative of the blood flow in the tissue. The heated device and thermocouple effectively act as a flowmeter for determining the blood flow as a function of the rate at which heat is carried away from the tissue.

Heated probes and thermocouples used for the determination of blood flow were first introduced by F. A. Gibbs in 1933 for the purpose of measuring flow in blood vessels. Gibbs' experiment is described in *Proc. Soc. Exptl. Biol. Med.* 31; 141–147, 1933, entitled, "A thermoelectric blood flow recorder in the form of a needle." Heated probes and thermocouples were later used as flowmeters by C. F. Schmidt and J. C. Pierson for measuring blood flow in solid organs. Schmidt's and Pierson's efforts are described in the *Am. J. Physiol.*, 108; 241, 1934, entitled, "The intrinsic regulation of the blood flow of medulla oblongata." Further investigation by J. Grayson and his colleagues described in *Nature* 215: 767–768, 1967, entitled, "Thermal Conductivity of Normal and Infarcted Heart Muscle," demonstrated that a heated probe with a thermocouple could be used in accordance with a certain relation, known as Carslaw's equation, to measure the thermal conductivity (k) of any solid, semisolid, or liquid in which the heated probe and thermocouple were inserted. Carslaw's equation is discussed in detail in the *Journal of Applied Physiology*, Vol 30, No. 2, February 1971, in an article entitled, "Internal Calorimetry Assessment of Myocardial Blood Flow and Heat Production."

A heated coil about a themistor may also by used as an effective flowmeter as described in a Technical Note entitled, "Thermal Transcutaneous Flowmeter," by D. C. Harding, et al., published in *Med. & biol. Engng.*, Vol. 5, 623–626, Pergamon Press, 1967, Printed in Great Britain.

"Heated" thermocouples or thermistors used in flowmeters, function to provide heat essentially by conduction to the tissue in immediate contact with the heating device, and measure the temperature of that tissue. Determination of fluid (blood) perfusion heretofore was limited by the heating of tissue essentially in contact with a heated device.

SUMMARY OF THE INVENTION

According to the invention, fluid perfusion of tissue is determined by measuring the thermal conductivity of the tissue by the steps of irradiating the tissue with a microwave signal having a predetermined repetition rate, amplitude and frequency, to elevate the temperature of a volume of the tissue to a predetermined temperature and measuring the rate of decay of the temperature of tissue, which decay is indicative of thermal conductivity of the volume of tissue and thus the fluid perfusion of the volume of tissue.

DESCRIPTION OF THE PREFERRED EMBODIMENT

Figure 1:
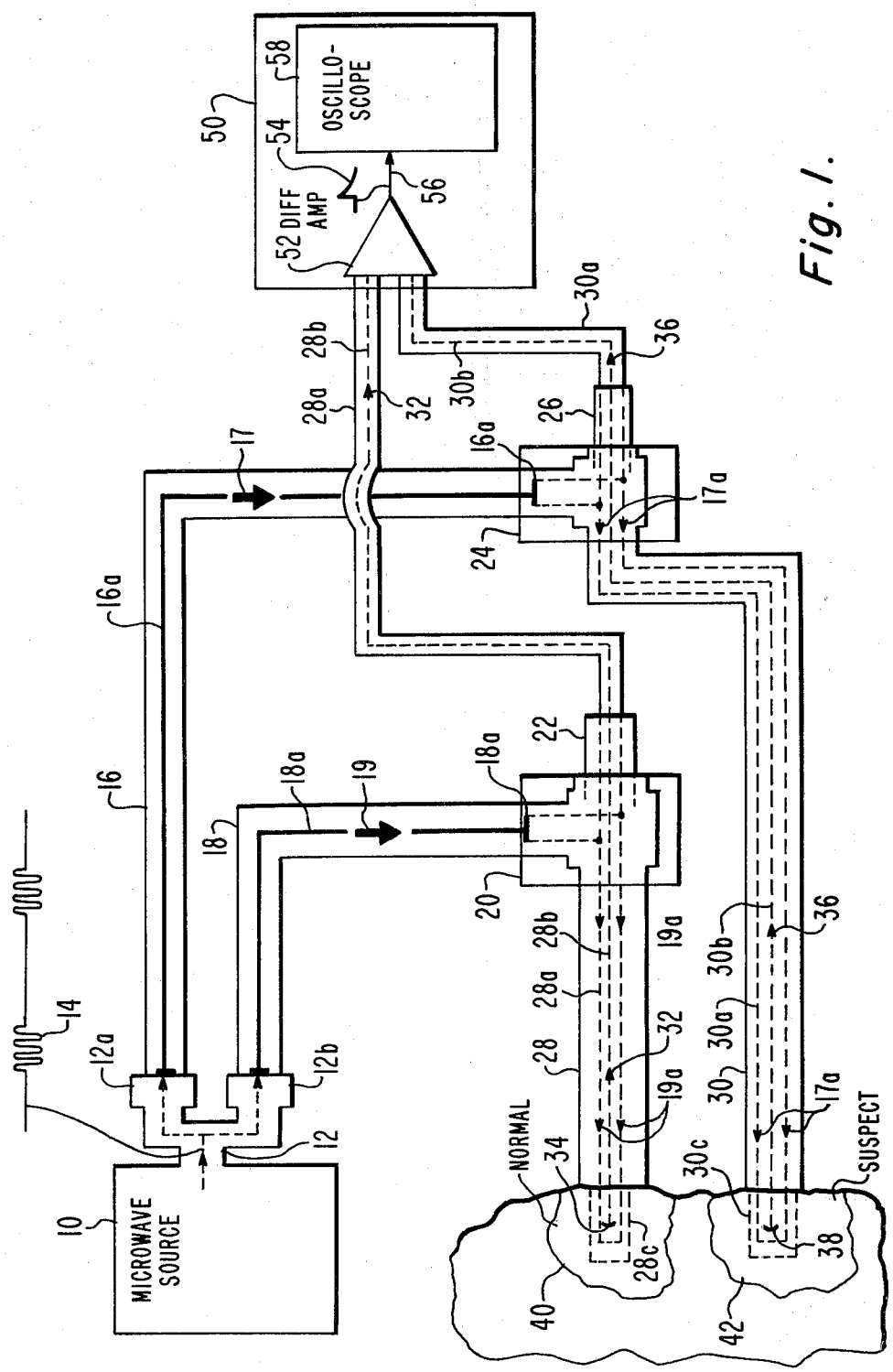
FIG. 1 is a block schematic of an apparatus useful in practicing one embodiment of the invention.

As shown in FIG. 1, a microwave source 10 provides a pulsed microwave signal 14 for irradiation of tissue 40 and 42. Tissues 40 and 42 may be, in practice, "normal" and "suspect" tissues, respectively, as will be discussed later. Signal 14 is typically a two watt pulsed microwave signal at 2.54 gigahertz, having a repetition rate of 20 pulses per minute each pulse having a duration of one (1) second. Signal 14 is coupled to coaxial cables 16 and 18 via a conventional 3 db power splitter 12 so that the power of signal 14 is substantially divided, in an equal manner, between coaxial cables 16 and 18. Coaxial cable 16 couples signal 14, in the direction of arrows 17 and 17a, to tissue 42 via a right angle connector 24 and a coaxial applicator 30. Similarly, coaxial cable 18 couples signal 14, in the direction of arrows 19 and 19a, to tissue 40 via a right angle connector 20 and a coaxial applicator 28. The coaxial applicators 28 and 30 may be of a type described in the above identified U.S. Patent application of R. W. Paglione. Suitable right angle connectors 20 and 24 are Model 1307-5002 connectors manufactured by Omni-Spectra/Americon of Waltham, Mass., modified as right angle connector 20 and 24 as described in the aforementioned Paglione application.

Cable 16 is attached to connector 24 in a conventional manner so that its center conductor 16a can be inserted in connector 24. Center conductor 16a is then attached to a hollow center conductor 30a of applicator 30. Within the hollow center conductor 30a are a pair of thermocouple wires 30b formed at one end into a thermocouple 38 and connected at the other end to a differential amplifier 52 of recording means 50. Similarly, coaxial cable 18 is attached to the right angle connector 20 in a conventional manner so that its center conductor 18a is inserted into connector 20 and then attached to a hollow center conductor 28a of applicator 28. Within the hollow center conductor 28a are a pair of thermocouple wires 28b formed at one end into a thermocouple 34 and connected at the other end to another input of differential amplifier 52.

Hollow telescopic brass slideable tuner slugs 22 and 26 connected to right angle connectors 20 and 24, respectively, as described in the aforementioned Paglione application, are adjusted to reduce the reflections resulting from impedance mismatches. Tuner slug 22 reduces the reflections produced by the internal connections within connector 20 of cable 18 to applicator 28 and the extensions of thermocouple wires 28b within connector 20 and tuner 22. Similarly, tuner slug 26 reduces the reflections produced by the internal connections within connector 24 of cable 16 to applicator 30 and the extensions of thermocouple wires 30b within connector 24 and tuner 26. Adjustment of tuners 22 and 26 provides for efficient coupling of signal 14 to tissue 40 and 42 and decoupling of signal 14 from the thermocouple signals of wires 28b and 30b. Signal 14 is launched into tissue 40 via an unshielded end 28c of applicator 28. Similarly, microwave signal 14 of source 10 is launched into tissue 42 via an unshielded end 30c of applicator 30. Ends 28c and 30c may be of the type described in Paglione's aforementioned application. Ends 28c and 30c invasively positioned at the sites of the tissues 40 and 42 to be examined, respectively, are shown in FIG. 1. It should be noted, however, that invasive positioning is not necessary when the tissue to be examined is on the surface or located in an exposed or directly accessible body cavity. During the performance of open-heart surgery, for example, the heart to be examined having already been exposed, unshielded ends 28c and 30c may be positioned at the sites without penetration. Accordingly, a possible traumatic penetration of the heart tissue is obviated.

Ends 28c and 30c function as monopole antennas converting the microwave signal 14 into electromagnetic fields within tissues 40 and 42, respectively. The ends 28c and 30c operate a predetermined frequency which defines the length of the shield that should be removed from the coaxial applicator. The portion of the shield removed to form the unshielded ends 28c and 30c determines whether the antenna functions as a directional or an omnidirectional antenna. The manner in which such an applicator is fabricated is described in the aforementioned application of Paglione.

Positioned at the tip of the unshielded end 28c is a themocouple 34 within hollow center conductor 28a and similarly, positioned at the tip of unshielded end 30c is a thermocouple 38 within hollow center conductor 30a. Thermocouples 34 and 38 are suitably electrically isolated, 304SS (stainless steel) sheathed, copper-constantum, Model Number SCPSS-020U-6, manufactured by Omega Engineering, Inc. of Waltham, Mass. If desired, a suitable platinum-platinum rhodium alloy, characteristically inert in the tissue environment, may be used as the temperature sensor element of thermocouples 34 and 38. However, the use of platinum-platinum rhodium in place of copper-constantum reduces the temperature response time of the coaxial applicators 28 and 30. As will be explained hereinafter in detail, the microwave signal 14 heats tissue volumes 40 and 42 by irradiation and the ambient temperatures of the irradiated volumes 40 and 42 about ends 28c and 30c, respectively, are measured by thermocouples 34 and 38. Thermocouples 34 and 38 develop d.c. voltages which are respectively coupled to differential amplifier 52, in the direction of arrow 32, via the thermocouple wires 28b and to differential amplifier 52, in the direction of arrow 36, via the thermocouple wires 30b. Differential amplifier 52 is suitably a type RCA CA-741 amplifier. Amplifier 52 is one element of recording means 50. Recording means 50 further comprises an oscilloscope 58. The d.c. voltages generated by thermocouples 34 and 38 are coupled to amplifier 52 which generates a signal 54 respresentative of the d.c. voltage difference between thermocouples signals of 34 and 38. The output signal 54 is coupled to oscilloscope 58 via signal path 56. Amplifier 52 functions in a conventional manner well known in the art and its operation is therefore not discussed further.

The apparatus, hereinbefore described is used to determine the rate of fluid flow through a volume of tissue. The particular fluid flow that is to be discussed hereinafter is blood flow. However, it should be understood that the invention may be used to determine the rate of flow of any fluid used for diagnostic purposes moved or moving through a volume of tissue. The rate of blood flow through tissue is indicative of the viability of the tissue. The rate of blood flow through tissue, hereinafter to be described as blood perfusion, is a means for determining if a tissue is normal or if it is ischemic, that is, if the tissue is abnormal.

In operation, when it is desired to examine the blood perfusion of subcutaneous tissue, the coaxial applicators 28 and 38 are inserted into tissue sites 40 and 42, respectively, at a fairly shallow depth. Microwave signal 14 penetrates tissues 40 and 42 to a depth dependent upon the nature of tissues 40 and 42 (fat, muscle, etc.), the frequency of signal 14, the irradiation pattern of signal 14 and the depth of insertion of ends 28c and 30c into tissues 40 and 42, respectively. The depth of insertion of ends 28c and 30c is dependent on the physical parameters of the tissues to be examined. For example, if it is desired to examine a muscular organ of a person, such as the heart of an adult, an insertion depth of ends 28c and 30c may be in the order of 5 mm. It should be noted that in certain medical procedures, penetration of the heart is indicated, whereas in other procedures, penetration of the heart would be proscribed.

As previously explained, ends 28c and 30c may be formed to provide either an omnidirectional or a directional antenna. If it is desired to confine the microwave signal 14 to a particular direction for irradiating tissues 40 and 42, ends 28c and 30c may be formed by a reflection to provide a directional antenna. Conversely, ends 28c and 30c may be formed to provide an omnidirectional antenna without a reflector for irradiating tissues 40 and 42 in all directions about ends 28c and 30c, respectively. Microwave signal 14 launched from ends 28c and 30c irradiates volumes of tissues 40 and 42, respectively, thereby elevating the temperature of volumes of tissues 40 and 42. The dimensions and the shape of the irradiated volumes are dependent on the parameters previously described for depth of penetration into tissues 40 and 42 which parameters are: the type of tissue, the frequency of signal 14, the irradiation pattern of signal 14, and the depth of insertion of ends 28c and 30c into tissues 40 and 42 respectively. A typical irradiated volume of tissue such as volume 40 or 42, is in the order of one cubic centimeter. The amplitude (i.e. power) of microwave signal 14 determines the intensity of the irradiation applied to tissues 40 and 42.

The temperature elevation of the volume of tissues 40 and 42 responsive to the microwave signal irradiation should not be so great as to damage or injure the tissues. Moreover, the tissue should not be heated so much as to dilate the blood vessels within the tissue, since such dilation may artificially affect the blood perfusion within the tissue and thereby preclude an accurate determination of the state of the tissue. Since the purpose of the process is diagnostic, it is critically important that the blood perfusion be determined accurately with a minimum of disturbance to the tissue. The increase in temperature within tissues 40 and 42 should be no more than 1° C., and preferably no less than 0.5° C. Typically, a two (2) watt microwave signal 14 at 2 GHz is adequate for developing such temperature increments.

Thermocouples 34 and 38, located at tissue sites 40 and 42 being examined, respectively, measure the ambient temperatures of the irradiated tissues 40 and 42 about the tips of coaxial applicators 28 and 30, respectively. Thermocouples 34 and 38, enclosed in sheaths within inner conductors 28a and 30a, respectively, are electrically isolated from microwave signal 14. This shielded isolation substantially prevents the thermocouples 34 and 38 from interfering with the irradiation signal 14. Furthermore, the shielding tends to prevent an undesirable "self-heating" of the thermocouple from affecting the measurement of the tissue temperature and disturbing the tissue environment. Thermocouples 34 and 38, directly connected to differential amplifier 52 from the sites of the tissues 40 and 42 being irradiated, continuously measure the temperature of tissue 40 and 42, respectively.

Irradiating signal 14 is periodically interrupted and the rates of the temperature decay of tissues 40 and 42 are determined. The ambient temperatures of the heated tissues 40 and 42, measured by thermocouples 34 and 38, respectively, when signal 14 is interrupted, function as initial temperatures for determining blood perfusion. The decay rate from these initial temperatures is indicative, as will be explained hereinafter, of blood perfusion through tissues 40 and 42. It should be noted that the initial temperature of tissues 40 and 42 need not be precisely determined to accurately evaluate blood perfusion. The rate of temperature decay is indicative of the blood perfusion through tissues 40 and 42. Although thermocouples 34 and 38 measure only the ambient temperatures adjacent the thermocouples within tissues 40 and 42 about ends 28c and 30c, respectively, which may not be the temperatures of all portions within the heated volumes of tissues 40 and 42, such sampled temperatures are, in practice, adequate to determine perfusion for relatively small volumes of tissue. It is assumed that all portions of small volumes of tissue will generally be heated to the same temperature. Furthermore, as will be explained, the temperatures measured need not be for the entire temperature change of the tissue of interest but may be merely a measurement of only a portion of the time period during which the tissue is cooled by the perfusion of blood. As will be explained, each of thermocouples 34 and 38 operates independently of the other effectively as flowmeters for assessing the rate of the flow of blood between tissues 40 and 42 by determining the rate of decay or loss of heat from the tissues. The loss of heat is determined by measuring the temperature of the heated tissues 40 and 42 after interruption of signal 14.

It has been previously demonstrated by J. Grayson, et al., in the aforementioned technical article entitled, "Thermal Conductivity of Normal and Infarcted Heart Muscle," that the fluid movements within an organ produce an apparent elevation in the thermal conductivity (k) which is approximately a linear function of flow within the organ. The rate at which the applied heat is dissipated by a tissue is indicative of blood perfusion whereby abnormal or ischemic tissues are manifested as having slower rates of heat dissipation than normal tissues.

The applied microwave signal 14 heating tissues 40 and 42 essentially define thermodynamically equivalent spheres of irradiated tissues 40 and 42. Such a spherical heat distribution lends itself to the aforementioned Carslaw's relation for analysis. In accordance with Carslaw's relation, in an infinite mass of muscle the relationship between thermal conductivity (k) and the temperature ($\theta$) to which the sphere of tissue is elevated is given by:

$$P = 4\pi r \theta k \qquad (1)$$

where P is the power applied to the tissues and r is the radius of the thermodynamically equivalent sphere.

The power P is derived from the microwave source, and is typically two watts. The elevated temperature ($\theta$) is 1° C. as explained hereinabove. The radius r, is dependent upon the type of tissue being examined, the frequency of microwave signal 14, and the irradiation pattern of signal 14. Typically a 2 GHz signal 14 provides a radius of 1 cm. below the surface of the tissues 40 and 42. Accordingly, a calculation for conductivity (k) from equation (1) provides an indication of the corresponding blood perfusion with a high degree of accuracy. A typical value for k is 0.001 cal/cm/sec/°C.

Referring again to the embodiment shown in FIG. 1, tissue 40 predetermined to be a normal tissue having known characteristics, is used as a reference to which a suspected abnormal tissue 42 is to be compared. The blood perfusion of tissue 42 is determined by comparing the d.c. signal of its thermocouple 38 with the d.c. signal of thermocouple 34 of tissue 40. The comparison begins after the applied microwave signal 14 is interrupted. The d.c. signals from thermocouples 34 and 38, at interruption, provide the initial temperatures of tissues 40 and 42. The initial temperatures at the start of the expected decay will reduce at the rate at which heat is removed from tissues 40 and 42. The heat removed from the tissues 40 and 42 is determined by the perfusion of blood through the respective tissues. The rate of cooling of the tissue adjacent to thermocouples 34 and 38 is indicative of the blood perfusion in the respectively heated tissues 40 and 42. The rate of temperature change in tissues 40 and 42 is indicative of the heat transfer property of tissues 40 and 42 and is therefore a means to determine the effective thermal conductivity in the tissue. To determine the extent of the perfusion of suspected tissue 42, the d.c. signal from thermocouple 38 indicative of the tissue temperature after irradiation and manifesting subsequent cooling by expected perfusion, is coupled to differential amplifier 52 which compares it with the d.c. signal from thermocouple 34 manifesting the temperature of reference tissue 40. Differential amplifier 52 generates a signal 54 on path 56 which is representative of the temperature difference between thermocouples 34 and 38. Differential signal 54 is coupled to oscilloscope 58 for display. For example, a positive d.c. voltage signal 54 is used to be indicative of a blood flow rate in the suspected tissue 42 having a perfusion of blood if any, that is inferior to that of the normal tissue 40. The larger the d.c. voltage of signal 54, the more restrictive is the blood flow of tissue 42. Signal 54 displayed on oscilloscope 58 is compared to a predetermined standard to evaluate if blood perfusion in suspicious tissue 42 is normal or abnormal. If the d.c. signal 54 is constant, the "suspected" tissue (42) is "normal."

It should now be appreciated that this invention provides an accurate determination of blood perfusion. A microwave signal 14 elevates the temperature of volumes of tissue 40 and 42 to be examined. Then the difference between the heat dissipation rates of tissues 40 and 42 indicative of the abnormal/normal blood perfusion through the volume of suspect tissue 42 is measured.

Figure 2:
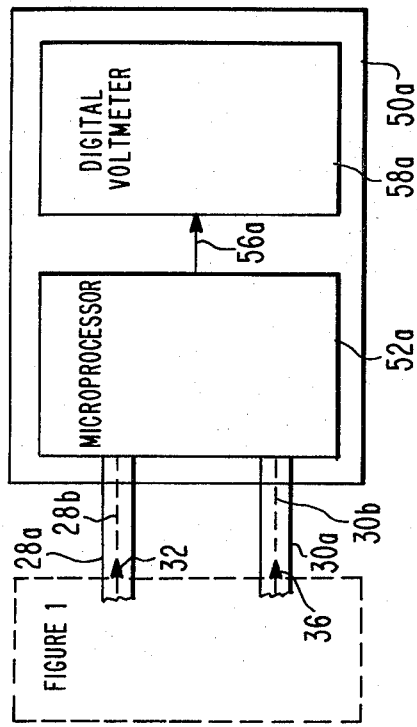
FIG. 2 is a block diagram of a conventional microprocessor 52a and digital voltmeter 58a for modifying the apparatus of FIG. 1.

In another embodiment of the invention, as shown in FIG. 2, a microprocessor 52a and digital voltmeter 58a are used rather than differential amplifier 52 and oscilloscope 58, respectively, shown in FIG. 1. Microprocessor 52a, and the digital voltmeter 58a provide an improvement in the analysis of the suspect tissue 42. Temperature changes experienced by tissues 40 and 42, after the interruption of microwave signal 14 are manifested as an exponentially decaying function. The rate of decay can be quite slow, requiring long observation periods to make a determination of the perfusion rate of the suspected tissue. For that reason, the analysis of the tissue can be improved by "linearization" of the temperature changes. "Linearization" is a sampling of two points separated by a predetermined time at the initial portions of the decay curve of the temperature of the suspect tissue. The two points connected by a straight line define a sample of the slope and thus a fair measure of the rate of the temperature decay. The sample of the slope is a good approximation of the blood perfusion of the tissue. A standard rate for a corresponding portion of the decay function may be catalogued and stored for reference purposes.

A microprocessor 52a, of a conventional type such as RCA COSMAC, maybe employed to "linearize" the temperature change of tissues 40 and 42. The microprocessor 52a receives d.c. signals from thermocouples 34 and 38 on a pair of thermocouple wires 28b and 30b, respectively. The microprocessor 52a samples each input d.c signal on paths 28b and 30b, periodically, e.g., once every millisecond, and sequentially. The sample time of each d.c. signal is determined by microprocessor 52a. Each of the d.c. signals on path 28b and 30b is converted into a digital value by a conventional analog-digital converter such as type ADC-82, manufactured by Burr Brown, Tucson, Arizona, located externally from microprocessor 52a.

Microprocessor 52a, by a suitable pre-programmed routine, performs the linearization of the temperature decay of tissue 42 with the knowledge of two temperature values of tissue 42: (1) the initial temperature of tissue 42 at the time signal 14 is removed from tissue 42, and (2) the temperature of tissue 42 after a predetermined time in the order of 1 second, following the interruption of signal 14. The initial temperature of tissue 42 is established by monitoring the digital value of signal on path 28b associated with the normal tissue 40. Microprocessor 52a monitors and processes the digital value of signal on path 28b and, upon the occurrence of a decreasing temperature value, microprocessor 52a uses the value of signal 30b at that time to determine the initial temperature of tissue 42. The microprocessor 52a waits the predetermined time and then reads the digital value of the signal on path 30b. Microprocessor 52a now has two values to determine the slope, or rate of decay of the temperature of tissue 42. Microprocessor 52a compares the slope that has been obtained with a desired value to determine the extent of the blood perfusion of suspected tissue 42. Microprocessor 52a then generates an electrical signal 56a to an output device such as digital voltmeter 58a to indicate the result of the analysis.

Figure 3:
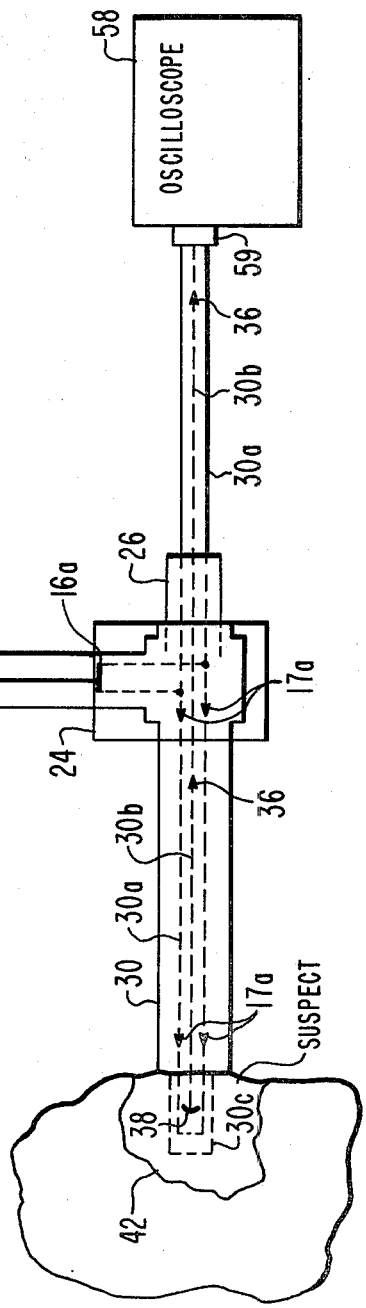
FIG. 3 is a block schematic of another apparatus for practicing another embodiment of the invention.

It should be recognized that although the use of two tissues 40 and 42 to determine tissue perfusion has been described, the perfusion of tissue may be determined by examining only tissue 42. Shown in FIG. 3, is a block diagram of an embodiment for examining only the tissue 42 to determine the blood perfusion of tissue 42 without a comparison to another tissue such as tissue 40. FIG. 3 is similar to FIG. 1 with the exception that the components used for heating and measuring tissue 40, and differential amplifier 52 are not needed. It will be appreciated that suitable switching networks provided with the apparatus of FIG. 1, may be used if desired to provide a single tissue analyzer as shown in FIG. 3. In FIG. 3, a coax connector 11 replaces power splitter 12 and connector 59 couples the inner conductor 30a and thermocouple wires 30b directly to oscilloscope 58.

The microwave heating of tissue 42 is accomplished by irradiating tissue 42 with the microwave signal 14, in the direction of arrows 17 and 17a, via coaxial cable 16 and coaxial applicator 30. As previously explained, the microwave signal 14 periodically irradiates tissue 42 via the unshielded end 30c of coaxial applicator 30. The d.c. voltage produced by thermocouple 38 is coupled directly to oscilloscope 58 via thermocouple wire 30b and connector 59 and thus displayed on oscilloscope 58. Affixed to the screen of oscilloscope 58 is a transparent tracing (not shown) showing the boundaries of a normal perfused tissue to which the display of the perfusion rate of tissue 42 is compared to determine if tissue 42 manifests a normally or an abnormally perfused tissue.

In still another embodiment, a plurality of reference tissue sites 40 are used to determine blood perfusion in a suspect tissue 42. This is achieved by the use of a plurality of coaxial applicators 28, right angle connector 20, tuner 22 and coaxial cable 18 connected in parallel, one each for each additional reference tissue site. In addition, the 3 db power splitter 12 shown in FIG. 1 is replaced with a suitable power splitter that divides the power of signal 14 evenly among the reference tissues and suspect tissue. In addition to tissue 40, the reference tissue sites (not shown) are herein termed 40a, 40b, 40c, etc. The reference d.c. voltage for the normal or reference tissues, to which the suspect tissue 42 d.c. voltage is to be compared is a composite reference, such as an arithmetic mean, of the d.c. voltages from tissue sites 40, 40a, 40b, and 40c. The arithmetic mean for four (4) tissues is expressed as $(40+40a+40b+40c)/4$. Microprocessor 52a, suitably programmed, performs the arithmetic mean processing. Microprocessor 52a periodically and sequentially scans and processes multiple thermocouple d.c. inputs from the normal tissues 40, 40a, 40b and 40c, computes the arithmetic mean of the d.c. voltages of the normal tissues and then compares the d.c. voltage arithmetic mean to the d.c. voltage from the suspect tissue 42. By using a plurality of normal or reference tissue sites (40, 40a, 40b and 40c, etc.) the number of data points for comparison with the suspect tissue 42 provides a smoothing effect to the temperature differences as will be described further. The use of the arithmetic mean reference signal reduces the probability of error that may occur if one of the normal tissues provides an erroneous temperature change. Thus, the smoothing effect improves the accuracy of the determination of the perfusion of the suspect tissue 42.

In still a further embodiment of the invention, more than one multiple coaxial applicators are distributed within the suspect tissue 42. Slow or poor blood perfusion in suspect tissue 42 may now be isolated to the portion of the tissue in which one of the multiple coaxial applicators experiencing a slow temperature decay may be located.

It should be appreciated that although the invention thus far described uses coaxial applicators having temperature sensing means at the site of the irradiated tissue, the essential functions performed by the coaxial applicator may be accomplished by other suitable means. The essential functions performed by the coaxial applicators are to couple a microwave signal for irradiation of a volume of tissue desired to be examined and then measure temperatures which are indicative of the rate of the temperature decay of the heated volume of tissue. The coupling function may be accomplished by a suitable applicator which irradiates the tissue desired to be examined with a microwave signal. The essential measuring function may be accomplished by a suitable temperature sensor that provides a measurement indicative of the rate of temperature decay of the heated volume. A suitable microwave applicator, positioned at the body surface for irradiating surface and subcutaneous tissue, in conjunction with a radiometer externally located which measures the temperature of the volume of heated tissue and thus capable of measuring the rate of temperature decay of the heated volume, are described in U.S. Patent Application Ser. No. 808,292 filed June 20, 1977.

This invention provides researchers in medical science with a method to accurately determine the blood perfusion through tissue. This method is especially needed during the recovery period for patients having had open-heart surgery and may be used by the attending medical staff to monitor subsequent blood restrictions.

What is claimed is:

1. A method of determining the fluid perfusion of tissue comprising the steps of:
   irradiating said tissue with microwave frequency signals to elevate a given volume of said tissue uniformly to a predetermined temperature, said signals having a predetermined rate, amplitude and frequency to uniformly heat said given volume;
   interrupting said irradiating signals; and
   measuring the rate of temperature decay of said volume of tissue from said predetermined temperature, said rate of temperature decay being indicative of the thermal conductivity of said volume of tissue and thus the fluid perfusion of said volume of tissue.

2. A method according to claim 1, wherein said tissue is suspected of being ischemic and is in an environment of other tissue having normal perfusion characteristics, further comprising the steps of:
   irradiating said normal tissue with said microwave frequency signals to elevate a volume of tissue equal to said given volume uniformly to said predetermined temperature;
   measuring the rate of temperature decay of said normal tissue; and
   comparing the rate of temperature decay of said suspect tissue relative to said normal tissue.

3. A method according to claim 1, wherein said temperature is elevated in the range of 0.5° c. to 1.0° C., whereby the blood vessels within said volume of said tissue are not substantially dilated.

4. A method according to claim 1, wherein the step of measuring the rate of temperature decay of said tissue comprises the steps of:
   recording said elevated temperature of said tissue;
   monitoring said temperature changes of said tissue for a predetermined time and then recording the temperature of said tissue; and
   determining the difference in temperature between said elevated temperature and said temperature at the end of said predetermined time to determine the rate of temperature decay during said predetermined time, said rate of decay being indicative of the thermal conductivity of said tissue and thereby the fluid perfusion of said tissue.

* * * * *

UNITED STATES PATENT AND TRADEMARK OFFICE
CERTIFICATE OF CORRECTION

PATENT NO. : 4,228,805

DATED : October 21, 1980

INVENTOR(S) : Arye Rosen and William P. Santamore

It is certified that error appears in the above-identified patent and that said Letters Patent is hereby corrected as shown below:

Col. 2, line 41, "1307" should be --1037--.

Signed and Sealed this

Twenty-seventh Day of January 1981

[SEAL]

Attest:

RENE D. TEGTMEYER

*Attesting Officer*     *Acting Commissioner of Patents and Trademarks*